United States Patent
Dutta et al.

(10) Patent No.: US 7,514,559 B2
(45) Date of Patent: Apr. 7, 2009

(54) CATALYST FOR SYNTHESIS OF 2- AND 4-PICOLINES

(75) Inventors: Pashupati Dutta, Jharkhand (IN);
Subhash Chandra Roy, Jharkhand (IN);
Shyam Kishore Roy, Jharkhand (IN);
Tarun Kanti Goswami, Jharkhand (IN)

(73) Assignee: Council of Scientific and Industrial Research, New Delhi (IN)

( * ) Notice: Subject to any disclaimer, the term of this patent is extended or adjusted under 35 U.S.C. 154(b) by 555 days.

(21) Appl. No.: 10/806,063

(22) Filed: Mar. 22, 2004

(65) Prior Publication Data

US 2005/0209458 A1    Sep. 22, 2005

(51) Int. Cl.
*C07D 213/12*    (2006.01)
(52) U.S. Cl. ................................ 546/253; 546/254
(58) Field of Classification Search ............ 546/253, 546/254
See application file for complete search history.

(56) References Cited

FOREIGN PATENT DOCUMENTS

EP    0 209 241    *    1/1987

OTHER PUBLICATIONS

Bamoharram, J of Molecular Catalysis A: Chemical 252 (2006), pp. 219-225.*
Roy, S. K. Studies in Surface Science and Catalysis, vol. 113 (Recent Advances in Basic and Applied Aspects of Industrial Catalysis), pp. 713-719, 1998.*

* cited by examiner

*Primary Examiner*—D. Margaret Seaman
(74) *Attorney, Agent, or Firm*—Ladas and Parry LLP

(57) ABSTRACT

The present invention provides a catalyst composite for the synthesis of 2- and 4-picolines and a process for the preparation thereof and use thereof for the synthesis of 2- and 4-Picolines.

16 Claims, No Drawings

CATALYST FOR SYNTHESIS OF 2- AND 4-PICOLINES

FIELD OF THE INVENTION

The present invention provides a catalyst composite for the synthesis of 2- and 4-picolines. The present invention also provides a process for the preparation of a catalyst useful for the synthesis of 2- and 4- Picolines. The present invention also provides a process for the preparation of 2- and 4-picolines using said novel catalyst. The present invention finds its usage in preparation of various intermediates for pharmaceuticals and agrochemicals. 2-Picoline is one of the main components in manufacture of pesticides. Major outlet for 4- Picoline is for the synthesis of 4-VinylPyridine and Iso-Nicotinic Acid Hydrazide (INH), an anti-tubercular drug.

BACKGROUND OF THE INVENTION

Commercially important sources of pyridine bases are tar and saturated liquor obtained by the carbonization of coal. However, the stringent specifications laid down for these products in pharmaceuticals and agricultural applications cannot be met from natural sources, namely from coal carbonization byproducts. Amongst the various synthetic routes, the reaction between acetaldehyde and ammonia is the most common one known in the prior art for making pyridine bases.

Acids have been used as catalysts or co-catalysts in a number of reactions. U.S. Pat. No. 2,186,392 reveals that ethanolamines may be produced from ammonia or a primary amine and ethylene oxide and a salt of a weak acid, such as ammonium carbonate, in the presence of an aliphatic radical which is positive with respect to hydrogen. German Patent 844,449 (CA 48:1429c) informs tertiary amines with hydroxyalkyl radicals may be made from ammonia, primary or secondary amines and an alkylene oxide at a temperature of from 30° C. to 60° C., with improved yields being possible if water or a weak acid is also present. British Patent No. 497, 093, (CA 36:4131-8) indicates that monoalkanolamines may be made from olefin oxides and ammonia in the presence of water and an acid.

The reaction of acetaldehyde or certain other low molecular weight aldehydes and ammonia either in the absence or presence of methanol and/or formaldehyde to yield pyridine and alkyl derivatives thereof has heretofore been carried out in the presence of amorphous silica-alumina composites containing various promoters. The yields of desired products using the latter catalysts have been poor. Alkylpyridines have also been synthesized, as reported in Advances in Catalysis, Volume 18, page 344 (1968) Academic Press, Inc., New York, N.Y., by passing gaseous acetaldehyde and ammonia over crystalline aluminosilicates, NaX and H-mordenite. While initial conversion utilizing these materials as catalysts was high, catalyst deactivation by coking was rapid, providing a commercially unattractive system, characterized by poor catalytic stability.

U.S. Pat. No. 4,220,783 provides a method for synthesizing pyridine or alkylpyridines by reacting ammonia and a carbonyl reactant which is an aldehyde containing 2 to 4 carbon atoms, a ketone containing 3 to 5 carbon atoms or mixtures of said aldehydes and/or ketones under effective conditions in the presence of a catalyst comprising a crystalline aluminosilicate zeolite having a silica to alumina ratio of at least about 12 and a constraint index within the approximate range of 1 to 12 and recovering from the resulting reaction mixture, a product containing at least one compound of pyridine or an alkylpyridine. Addition of methanol and/or formaldehyde to the feed improves selectivity to unsubstituted pyridine. The yields of desired products have been poor. Manufacture of pyridine bases by employing the catalyst causes environmental pollution because these routes use toxic $ThO_2$ and $CdO$. The catalyst preparation involves tedious method for the preparation of silica alumina gel.

OBJECTS OF THE INVENTION

The main object of the invention is to provide a catalyst suitable for the conversion of acetaldehyde and ammonia to 2- and 4-Picolines which obviates the drawbacks as detailed above.

Another object of the invention is to provide a stable catalyst for the conversion of acetaldehyde and ammonia.

Still another object of the invention is to provide a catalyst which is highly selective and active.

SUMMARY OF THE INVENTION

Accordingly the present invention provides a catalyst useful for synthesis of 2- and 4- Picolines which comprises a heteropoly acid selected from the group consisting of silicotungstic acid, phosphotungstic acid, phosphomolybdic acid and vanadotungstic acid provided on a support.

In one embodiment of the invention, the support is selected from the group consisting of silica gel, alumina, silica-alumina, clays and montmorillonite.

The present invention also provides a process for the preparation of a catalyst useful for the synthesis of 2- and 4-picolines, the process comprising dissolving a heteropoly acid in distilled water; mixing the resulting mixture with desired amount of a binder to obtain a slurry; stirring the slurry till uniform impregnation is achieved; drying the slurry in air at 200-250° C. for a time period in the range of 0.5 to 1.5 hours; further heating the slurry at a temperature in the range of 300 to 400° C. for time period in the range of 0.5 to 1.5 hours and cooling the resultant product to room temperature in a desiccator to get the desired catalyst.

In one embodiment of the invention the heteropoly acid is selected from the group consisting of silicotungstic acid, phosphotungstic acid, phosphomolybdic acid and vanadotungstic acid.

In another embodiment of the invention the binder is selected from the group consisting of silica, alumina, silica-alumina, clays and montmorillonite.

In another embodiment of the invention, the heteropoly acid is dissolved in distilled water in a ratio of 0.5:4.5 (w/w).

In another embodiment of the invention, the binder comprises silica gel of mesh size 6-14.

In yet another embodiment of the invention, the slurry is stirred for a time period in the range of 30-40 minutes.

The present invention also provides for a process for the preparation of 2- and 4-picolines which comprises reacting acetaldehyde and ammonia under heat in the presence of a catalyst comprising a composite of a heteropolyacid impregnated on a support, the catalyst being present in an amount in the range of 5 to 15 wt %, and separating the 2- and 4-picoline formed.

In one embodiment of the invention, the acetaldehyde and ammonia are taken in a ratio of 0.8 to 1.2 (w/w) and are reacted at a temperature in the range of 300 to 500° C.

In another embodiment of the invention, the reaction is carried out in a glass reactor.

In yet another embodiment of the invention, the weight hourly space velocity of the acetaldehyde and ammonia is maintained in the range of 0.1 to 10 g/g of catalyst (preferably 1 to 3).

In yet another embodiment of the invention, the 2- and 4-picolines are separated by fractional distillation.

DETAILED DESCRIPTION OF THE INVENTION

The present invention provides a catalyst useful for synthesis of 2- and 4- Picolines which is prepared by dissolution of a heteropoly acid in distilled water in a suitable proportion in the range of 0.5:4.5 (w/w). The resulting mixture is then mixed with desired amount of a binder such as silica gel (having mesh size 6-14) and the slurry obtained stirred for a time period in the range of 30-40 minutes to get a uniform impregnation. After uniform impregnation is obtained, the slurry is first dried in air at a temperature in the range of 200-250° C. for a time period in the range of 0.5 to 1.5 hours and then further heated at temperature in the range of 300 to 400° C. for time period in the range of 0.5 to 1.5 hours. The resulting product is then cooled to room temperature in a desiccator to get the desired catalyst.

The heteropoly acid is selected from silicotungstic acid, phosphotungstic acid, phosphomolybdic acid and vanadotungstic acid and the binder is from silica, alumina, silica-alumina, clays, montmorilonite.

The catalyst obtained is useful for the synthesis of 2- and 4-picolines by heating acetaldehyde and ammonia in a ratio of 0.8 to 1.2 (w/w) at a temperature in the range of 300 to 500° C. The amount of the catalyst is in the range of 5 to 15 wt % and the reaction is carried out preferably in a glass reactor. The reaction is carried out by maintaining weight hourly space velocity of the feed, comprising of acetaldehyde and ammonia, between 0.1 to 10 g/g of catalyst (preferably 1 to 3). The pyridine bases and product obtained are analyzed by by known spectrochromatographic methods and the pyridine bases separated from the desired products by conventional fractional distillation.

The novelty of the present invention lies in preparing the catalyst for the conversion of acetaldehyde and ammonia to 2- and 4-picolines in an ecofriendly manner. This process avoids environmental pollution in comparison to prior art processes.

The following examples are given by way of illustration of the present invention and should not be construed to limit the scope of the present invention.

EXAMPLE-1

Preparation of the Catalyst: Silica gel, mesh size 6-14, was used as the silica support.

Phosphotungstic acid (10 g) was dissolved in water (25 ml) and the solution was mixed with silica gel (100 g). The slurry was stirred to get a uniform impregnation, dried in air at 200-250° C. for one hr., then at 400° C. for one hour, and finally cooled to room temperature in a desiccator. This catalyst was used for the reaction between acetaldehyde and ammonia.

The experiment was carried out in a downward flow glass reactor of internal diameter of 2 cm and of sufficient length which was kept in a furnace of length 32 cm. In the middle of the reactor was kept the catalyst (10 g) made and heated to 380° C. with the help of a tubular electrical furnace. Acetaldehyde was fed at a rate of 9.5 ml/hr and ammonia was fed at a rate 60 ml/min. The products formed in 2 hours were condensed in an ice cooled receiver, weighed and analyzed by gas chromatography (fitted with FID using 2 m×3 mm SS column containing 30% glycerol on chromosorb-p. The column temperature was maintained at 135° C. and nitrogen flow was 30 ml/min.) Pure standard substances were used for calibration. Conversion of acetaldehyde to picolines was found to be 50-60%.

EXAMPLE-2

Preparation of the Catalyst: Silica gel, mesh size 6-14, was used as the silica support.

Silicotungstic acid (10 g) was dissolved in water (25 ml) and the solution was mixed with silica gel (100 g). The slurry was stirred to get a uniform impregnation, dried in air at 225° C. for one hr., then at 400° C. for one hour, and finally cooled to room temperature in a desiccator. This catalyst was used for the reaction between acetaldehyde and ammonia.

The experiment was carried out in a downward flow glass reactor of internal diameter of 2 cm and of sufficient length which was kept in a furnace of length 32 cm. In the middle of the reactor was kept the catalyst (10 g) made and heated to 400° C. with the help of a tubular electrical furnace. Acetaldehyde was fed at a rate of 9.5 ml/hr and ammonia was fed at a rate 60 ml/min. The products formed in 2 hours were condensed in an ice cooled receiver, weighed and analyzed by gas chromatography (fitted with FID using 2 m×3 mm stainless steel column containing 30% glycerol on chromosorb-p. The column temperature was maintained at 135° C. and nitrogen flow was 30 ml/min.) Pure standard substances were used for calibration. Conversion of acetaldehyde to picolines was found to be 55%.

EXAMPLE-3

Preparation of the Catalyst: Silica gel, mesh size 6-14, was used as the silica support.

Vanadotungstic acid (10 g) was dissolved in water (25 ml) and the solution was mixed with silica gel (100 g). The slurry was stirred to get a uniform impregnation, dried in air at 210° C. for one hr., then at 400° C. for one hour, and finally cooled to room temperature in a desiccator. This catalyst was used for the reaction between acetaldehyde and ammonia.

The experiment was carried out in a downward flow glass reactor of internal diameter of 2 cm and of sufficient length which was kept in a furnace of length 32 cm. In the middle of the reactor was kept the catalyst (10 g) made and heated to 370° C. with the help of a tubular electrical furnace. Acetaldehyde was fed at a rate of 9.5 ml/hr and ammonia was fed at a rate 60 ml/min. The products formed in 2 hours were condensed in an ice cooled receiver, weighed and analyzed by gas chromatography (fitted with FID using 2 m×3 mm stainless steel column containing 30% glycerol on chromosorb-p. The column temperature was maintained at 135° C. and nitrogen flow was 30 ml/min.) Pure standard substances were used for calibration. Conversion of acetaldehyde to picolines was found to be 70%.

The main advantages of the present invention are:
1. The process is very simple and economic.
2. The catalyst preparation avoids tedious methods in comparison to prior art processes

We claim:

1. A process for the preparation of 2- and 4- picolines which comprises (a) providing a heteropoly acid catalyst comprising vanadotungstic acid provided on a support, and (b) reacting acetaldehyde and ammonia under heat in the presence of the catalyst, the catalyst being present in an amount in the range of 5 to 15 wt %, and (c) separating the 2- and 4- picoline formed.

2. A process as claimed in claim 1 wherein the acetaldehyde and ammonia are taken in a ratio of 0.8 to 1.2 (w/w) and are reacted at a temperature in the range of 300 to 500° C.

3. A process as claimed in claim 1 wherein the reaction is carried out in a glass reactor.

4. A process as claimed in claim 1 wherein weight hourly space velocity of the acetaldehyde and ammonia is maintained in the range of 0.1 to 10 g/g of catalyst.

5. A process as claimed in claim 4 wherein the weight hourly space velocity of the acetaldehyde and ammonia is maintained in the range of 1 to 3 g/g of the catalyst.

6. A process as claimed in claim 1 wherein the the 2- and 4- picolines are separated by fractional distillation.

7. A process as claimed in claim 1 wherein the binder is selected from the group consisting of silica, alumina, silica-alumina, clays and montmorillonite.

8. A process as claimed in claim 1 wherein the binder comprises silica gel of mesh size 6-14.

9. A process as claimed in claim 2, wherein the acetaldehyde and ammonia are reacted at a temperature of 300° C.

10. A process as claimed in claim 1, which consists essentially of steps (a)-(c).

11. A process as claimed in claim 1, wherein the catalyst provided in step (a) is prepared by dissolving vanadotuncistic acid in distilled water; mixing the resulting mixture with a desired amount of a binder to obtain a slurry; stirring the slurry till uniform impregnation is achieved; drying the slurry in air at 200-250° C. for a time period in the range of 0.5 to 1.5 hours; further heating the slurry at a temperature in the range of 300 to 400° C. for time period in the range of 0.5 to 1.5 hours and cooling the resultant product to room temperature in a desiccator to get the catalyst.

12. A process as claimed in claim 1, wherein the heteropoly acid catalyst is provided in step (a) by dissolving vanadotuncistic a acid in distilled water; mixing the resulting mixture with a desired amount of a binder to obtain a slurry; stirring the slurry till uniform impregnation is achieved; drying the slurry in air at 200-250° C. for a time period in the range of 0.5 to 1.5 hours; further heating the slurry at a temperature in the range of 300 to 400° C. for time period in the range of 0.5 to 1.5 hours and cooling the resultant product to room temperature in a desiccator to get the catalyst.

13. A process as claimed in claim 12 wherein the binder is selected from the group consisting of silica, alumina, silica-alumina, clays and montmorillonite.

14. A process as claimed in claim 12 wherein the vanadotungstic acid is dissolved in distilled water in a ratio of 0.5:4.5 (w/w).

15. A process as claimed in claim 12 wherein the binder comprises silica gel of mesh size 6-14.

16. A process as claimed in claim 12 wherein the slurry is stirred for a time period in the range of 30-40 minutes.

* * * * *